(12) United States Patent
Anker et al.

(10) Patent No.: US 11,013,410 B2
(45) Date of Patent: May 25, 2021

(54) BLINKING MULTIPLEXED LED STRAIN AND CHEMICAL SENSORS FOR IMPLANTED MEDICAL DEVICES

(71) Applicants: Jeffrey N. Anker, Greenville, SC (US); Donald W. Benza, Aiken, SC (US)

(72) Inventors: Jeffrey N. Anker, Greenville, SC (US); Donald W. Benza, Aiken, SC (US)

(73) Assignee: Aravis BioTech, LLC, Greenville, SC (US)

( * ) Notice: Subject to any disclaimer, the term of this patent is extended or adjusted under 35 U.S.C. 154(b) by 18 days.

(21) Appl. No.: 15/913,332

(22) Filed: Mar. 6, 2018

(65) Prior Publication Data

US 2018/0249909 A1 Sep. 6, 2018

Related U.S. Application Data

(60) Provisional application No. 62/467,539, filed on Mar. 6, 2017.

(51) Int. Cl.
*A61B 5/00* (2006.01)
*G01F 15/06* (2006.01)
*A61B 5/145* (2006.01)
*A61B 5/103* (2006.01)

(52) U.S. Cl.
CPC .......... *A61B 5/0031* (2013.01); *A61B 5/0017* (2013.01); *A61B 5/4504* (2013.01); *A61B 5/686* (2013.01); *G01F 15/066* (2013.01); *A61B 5/1038* (2013.01); *A61B 5/14539* (2013.01); *A61B 5/14542* (2013.01);
(Continued)

(58) Field of Classification Search
CPC ... A61B 5/0015; A61B 5/0017; A61B 5/0026; A61B 5/0028; A61B 5/0031; A61B 5/4504; A61B 5/145; A61B 5/1455; A61B 5/14539; A61B 5/6846; A61B 5/6847; A61B 5/686; A61B 5/72; A61B 5/7228
See application file for complete search history.

(56) References Cited

U.S. PATENT DOCUMENTS

| 8,320,983 | B2 * | 11/2012 | Martini ............... | A61B 5/1459 600/316 |
| 2002/0026108 | A1 * | 2/2002 | Colvin, Jr. ........... | A61B 5/0031 600/316 |

OTHER PUBLICATIONS

Benza et al., X-ray excited luminescent chemical imaging (XELCI) for non-invasive imaging of implant infections, Pro SPIE Int Soc Opt Eng., 2017, 1008, 1-15.

(Continued)

*Primary Examiner* — Eduardo C Robert
*Assistant Examiner* — Christina Negrellirodriguez
(74) *Attorney, Agent, or Firm* — Dinsmore & Shohl LLP

(57) ABSTRACT

Implantable sensors are described that can be utilized in conjunction with orthopedic implants for monitoring fracture healing and detecting local chemical concentrations to detect and monitor implant associated infection. The sensors can include strain gauges, electrochemical, or spectrochemical sensors that can be read transdermally using a single photodetector. Sensors can be affixed to implantable support devices so as to non-invasively monitor the effect of load on the implant to provide a quantitative assessment of when a fracture is sufficiently healed to allow safe weight-bearing upon the limb. Alternatively, sensors can monitor the local concentration of infection biomarkers, for instance to monitor the implant area for early stage infection.

19 Claims, 5 Drawing Sheets

(52) U.S. Cl.
CPC ........... *A61B 5/4523* (2013.01); *A61B 5/4533* (2013.01); *A61B 2562/08* (2013.01); *A61F 2250/0002* (2013.01)

(56) References Cited

OTHER PUBLICATIONS

Pelham et al., Implantable strain sensor to monitor fracture healing with standard radiography, Scientific Reports, May 4, 2017, 7: 1489, 1-8.
Quaranta et al., Indicators for optical oxygen sensors, Bioanal Rev, 2012, 4:115-157.

* cited by examiner

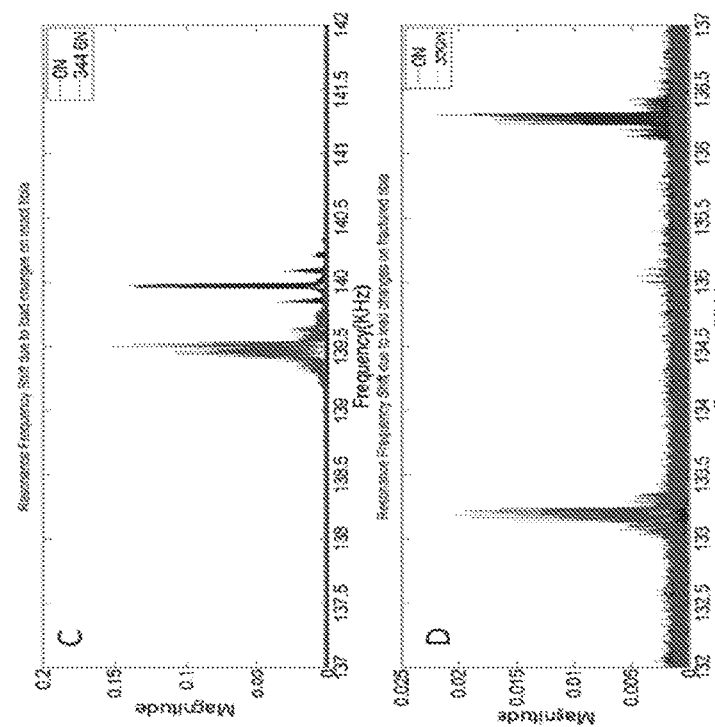
FIG. 2C
FIG. 2B
FIG. 2A
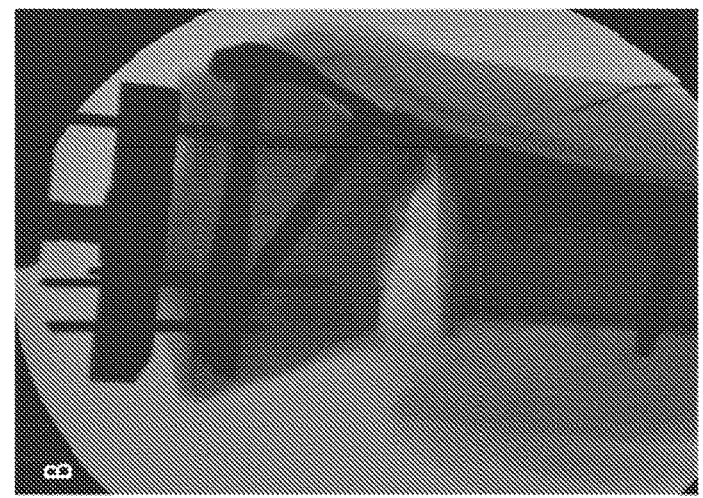
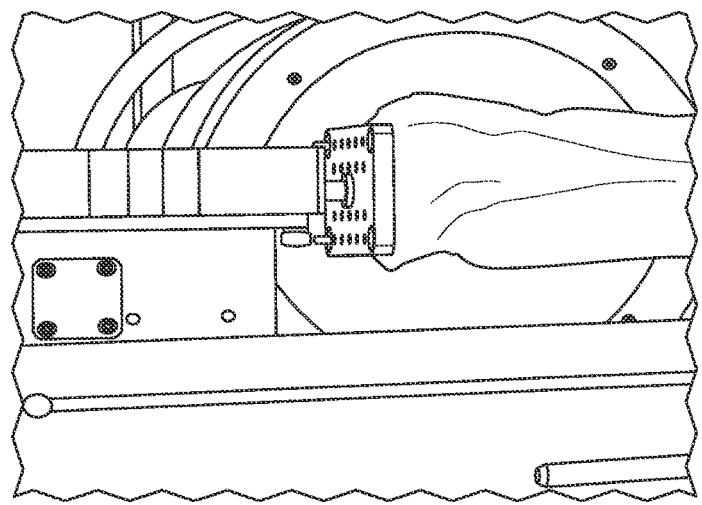
FIG. 2D

BLINKING MULTIPLEXED LED STRAIN AND CHEMICAL SENSORS FOR IMPLANTED MEDICAL DEVICES

CROSS REFERENCE TO RELATED APPLICATION

This application claims filing benefit of U.S. Provisional Patent Application Ser. No. 62/467,539 having a filing date of Mar. 6, 2017, which is incorporated herein by reference in its entirety.

STATEMENT REGARDING FEDERALLY SPONSORED RESEARCH OR DEVELOPMENT

This invention was made with government support under National Science Foundation Grant No. CHE-1255535 and Grant No. GM103444 awarded by the National Institutes of Health. The government has certain rights in the invention.

BACKGROUND

Over 28 million musculoskeletal injuries are treated annually in the U.S. including 2 million fracture fixation surgeries. Of these, tibia fractures are the most common long bone fracture. Unfortunately, such fractures are frequently associated with complications (delayed union, non-union, and infection), particularly for severe trauma. For instance, non-union is a significant complication (approximately 100,000 injuries, 5% of all fixation surgeries in the U.S. go on to non-union and a similar number result in infection), with even higher rates for severe trauma. Infection at the site of orthopedic surgery is an on-going issue and, while the incidence has been reduced due to improvements in both surgical and post-operative procedures, its prevalence is still unacceptably high. Such complications can lead to long-term or even permanent disability or death and are responsible for significant direct and indirect health care costs.

While a variety of supporting implants, physical therapy regimes, and adjunct therapies are available if healing is known to be poor, poor healing is often undetected. Physicians routinely acquire X-ray images as part of diagnosis and evaluation; although these images can show the hardware and fracture callus, they do not measure mechanical properties of the fracture and cannot detect early-stage infection. 3-dimensional CT images are better at indicating bone density and determining if union has occurred, but are expensive, expose the patient to significant radiation doses, and are imperfect, especially when allografts are used.

When considering localized infection, external visualization techniques provide little or no clues, particularly in early stages of infection. Unfortunately, infection at orthopedic trauma sites are generally not diagnosed until after the infection has spread and symptoms have become systemic. Bacteria which colonize on implant hardware can form biofilms which are highly resistant to antibiotics and the host's immune system. Once the infection has established, it is difficult to eradicate, and the hardware often needs to be surgically removed to treat the infection. Early detection is key to reducing morbidity, mortality, and costs associated with surgical interventions and associated factors to remove and replace hardware.

The lack of widely applicable tests to assess bone health such as load bearing state and early stage infection presents a major challenge for physicians and patients. Infection at implant sites can require additional surgery or even become life-threatening when diagnosis is delayed.

Weight bearing before the fracture callus is sufficiently strong carries risk of re-fracture and/or hardware failure. On the other hand, unnecessary delay in weight bearing can hamper rehabilitation and is highly costly in terms of lost days of activity. Studies have shown that when the fractured bone has at least 25% of the bending stiffness of intact bone, weight bearing rarely leads to re-fracture or hardware failure. For externally fixed devices, percutaneous pins can be directly loaded to assess stiffness. When testing is carried out and this 25% threshold is used, most patients begin weight bearing an average of 2.3 weeks earlier than average. Load testing on externally fixated devices can likewise identify patients with delayed and non-union for weight bearing restrictions and additional interventions.

Most orthopedic surgeries involve internal fixation, which require either a percutaneously connected gauge or remote measurements to assess load bearing capabilities during healing. A percutaneously connected strain gauge is impractical for patients and presents a number of safety challenges. A variety of remote interrogation methods based upon implanted wireless devices, ultrasound, vibrational analysis, and other approaches have been examined for non-invasive measurement of strain on orthopedic implants, but these generally require significant development as well as equipment and/or expertise currently unavailable to most care givers.

What are needed in the art are implantable sensors for use in conjunction with orthopedic implants that can be easily read by conventional non-invasive methods to assess local conditions and bone health at the local site. In particular, what are needed are sensors capable of assessing strain under load and/or early stage signs of infection and thereby to determine a current state of bone health. For instance, a sensor locatable on bone fixation devices that can assess health and healing in the local area of an orthopedic implant by use of conventional radiography methods would be of great benefit.

SUMMARY

According to one embodiment, a device is described, configured to attach to the surface of or integrated within an implanted medical device (e.g., orthopedic plate) and optically report local conditions. The device includes a light emitting diode (LED), power source (e.g. battery, capacitor, or inductive coupling), a method to switch the device on (e.g. a reed switch, or phototransistor, or acoustic transducer) and sensor (e.g., pH indicator and/or foil-bound strain gauge).

Simple frequency-based readout of strain provides high accuracy. Multiple closely-spaced light emitting diodes (LEDs), each blinking at its own frequency allows multiple signals and references to be detected simultaneously using the same photodetector; use of a reference allows variation due to spectral distortion, and optical collection efficiency to be accounted for, in addition, multiple sensors can improve sensitivity/specificity for pathologies. Simple reed switch or phototransistor with band pass filter, or similar arrangement turns on the device at will conserving power. LEDs are encapsulated beneath epoxy, PDMS, or other material, insulating them from the tissue. Measurements can be performed on a cell phone.

Methods for using the sensors to determine the state of bone fracture healing also described. For instance, a method can include placing a fractured and orthopedically fixed bone under load (e.g. by standing on a leg, lifting an object of known weight, or using a limb to apply force to a scale and using the scale to set or determine the force applied). The bone can have affixed thereto an orthopedic fixation component (e.g., a fixation plate, rod, screw, etc.) that carries a sensor. A method can also include interrogating the sensor by placing the photodetector or photodetector-coupling optics in contact or proximity to the skin above the light source, and measuring the LED blinking pattern. Although stray optical signals are very unlikely to blink at the same rate as the LEDs, measurements performed in the dark will have less background and generally higher signal/noise.

In one embodiment, a method can determine local chemical concentrations near an implanted medical device. For instance, measuring local chemical concentrations could be useful for detecting and monitoring infection and inflammation. There are many potential biomarkers which can alone or in combination indicate local pathophysiology. These include, but are not limited to: local acidity (pH), oxygen, glucose, interleukins, C-reactive protein, leukocyte esterase, nitrite, and quorum sensing molecules. In the art, many indicator dyes and optical-sensing schemes have been developed to detect these analytes. However, it is challenging to measure local chemical concentrations through tissue, even if dyes are available because it is difficult to distinguish the sensor signal from background from the surrounding tissue and skin (such as absorption, scattering, and fluorescence). The invention uses implanted LEDs as a local light source to provide a low background signal from local absorptive indicators. These indicators can be applied as films or coating above the LED and alter the light intensity transmitted through them according to analyte concentration, ultimately altering the intensity of light passing through the skin. Although the light intensity also depends strongly upon the tissue absorption and optical collection efficiency, the invention provides a second light source in proximity to the first LED to serve as a reference to account for changes in optical collection efficiency. The light sources are spaced close enough together that light from each LED passes through essentially the same amount of tissue, and both have similar or identical wavelengths, the main difference arising from the indicator placed over the sensor LED. As those skilled in the art have observed, the light scatters and spreads out as it passes through tissue, with a point-spread function that is typically around the depth of the tissue being imaged through. Thus, if the sources are close together compared to the point-spread-function, then they will appear to be a single source. Although the two light sources have essentially the same wavelength and appear to be coming from essentially the same location, they can be separated if they are modulated at different frequencies by demodulating the signal. The ratio between signal passing through the indicator film and the reference can then be calculated and compared to a calibration to determine local chemical concentrations.

The invention is not limited to absorption-based dyes. For example, Another embodiment uses fluorescence emission from a sensor film loaded with a fluorescent indicator dye. An LED is used to excite fluorescence from the film at wavelength chosen to excite the fluorophore and generate an analyte-dependent fluorescence emission. A second LED with a wavelength similar to the fluorescence emission serves as a reference.

The optical signal could also be from other phenomena including cross-polarized signals to measure local strain from a photoelastic materials. The light from the LED would be polarized, and the signal passing through a photoelasitic material and then a cross-polarizer would depend upon the strain on the photoelastic material. In addition, scattering could be measured for determining purulence or turbidity in a joint fluid. Blue light could be directed through a pinhole, and red or near infrared fluorescent film placed near the pinhole so that blue light scattering close to the pinhole would illuminate the fluorophores and generate red or near infrared light, while light not rapidly scattered would move further into the tissue where it would be absorbed and not generate red or near infrared fluorescence.

Multiple LEDs can be used for detecting multiple analytes and references simultaneously. Though these local chemical and physical measurements, the local condition and pathophysiology at the implant surface can be determined (e.g., early detecting a local infection and monitoring fracture stiffness to track bone healing).

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 2A is a photograph of a plated human cadaver tibia.

FIG. 2B is a radiograph of a tibia after osteotomy.

FIG. 2C is a graphical depiction of a Fourier transform of a blinking signal showing primary blinking frequency with compressive load of 0 N and 350 N on intact tibia.

FIG. 2D is a graphical depiction of a Fourier transform of blinking signal showing primary blinking frequency with compressive load of 0 N and 350 N on fractured tibia.

FIG. 5A is a circuit schematic for one constantly on reference LED and one modulated LED.

FIG. 5B is a spectrum of reference LED bulb and modulated 460 nm blue-emitting LED bulb coated with oxygen-sensitive fluorescent dye, which is excited by the 460 nm light in (oxyphore G4 in polydimethylsiloxane polymer film) and is constant near infrared-emitting bulb (emitting primarily at 835 nm).

FIG. 5C is a waveform of luminescence between 800-813 nm including both the modulated fluorescence and constant reference.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to devices and methods for determining the local physiological conditions near an implanted medical device. More specifically, disclosed are sensors that can be utilized in conjunction with orthopedic implants that can provide information with regards to the ability of orthopedic tissue (e.g., bones, ligaments, tendons, etc.) to support a load and/or the presence of infection near an implant. Beneficially, the sensors provide a light source in the tissue, which is low background signal. Moreover, the sensors can be affixed to known implantable support devices (e.g., tibial plates, spinal inserts, screws, rods, pins, etc.) without excessive modification of the implants so as to non-invasively monitor the implant to provide a quantitative assessment of one or more characteristics in the local area of the implant.

In one embodiment, the sensor can be a strain sensor that can be utilized to determine when a damaged bone, joint, or soft orthopedic tissue is sufficiently healed to allow safe weight-bearing upon the limb. By measuring the change in strain between loaded and unloaded states, the stiffness of the structure can be determined. While the bulk of this application discusses utilization of disclosed sensors in conjunction with bones, it should be understood that disclosed sensors can be utilized in conjunction with other implanted medical devices and other tissues.

Figure 1A:
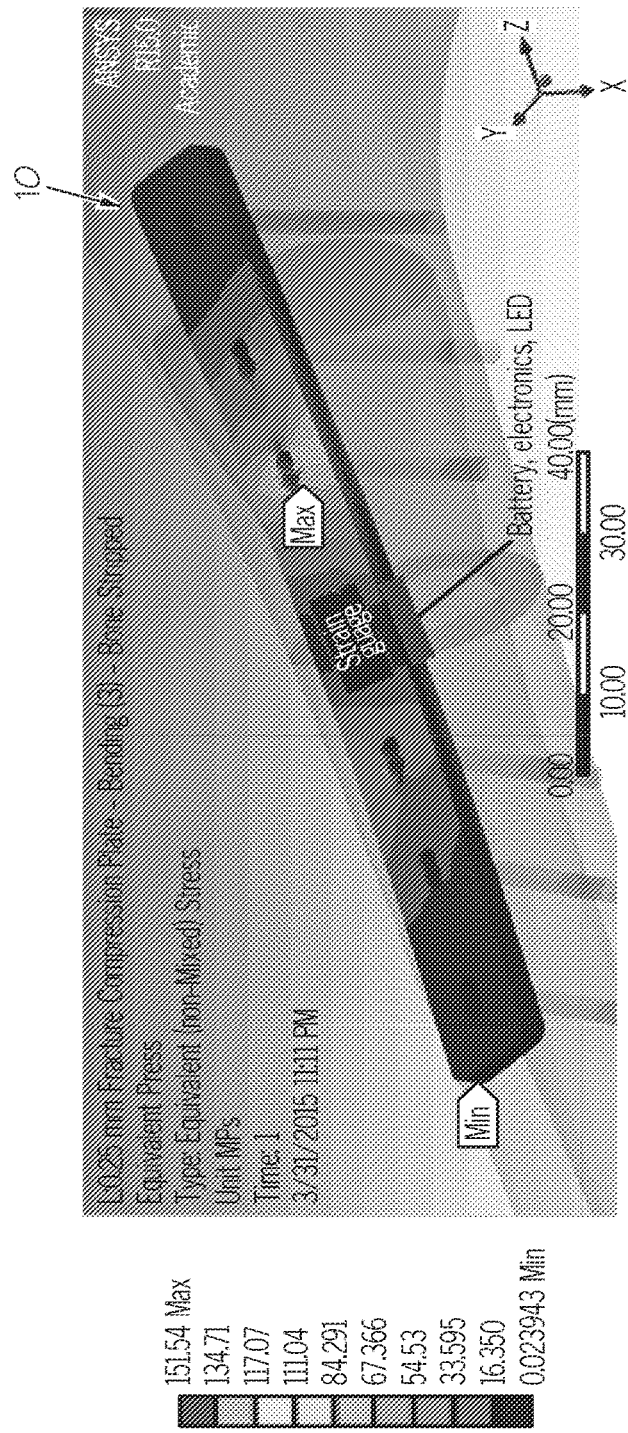
FIG. 1A illustrates a simulated strain pattern for a straight dynamic compression plate across a tibial fracture. The location of the strain gauge bound to the implant, and the battery and electronics on the side are indicated.
Figure 1B:
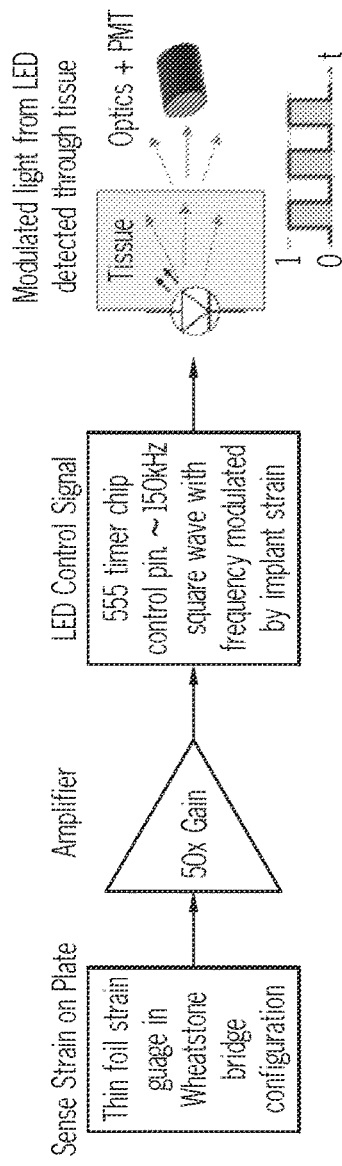
FIG. 1B is a schematic showing one embodiment of strain sensing electronics and LED output.

To illustrate, FIG. 1A schematically illustrates a fractured bone with an orthopedic fixation device affixed to the bone. The bone is a computational model of a tibia provided by Sawbones, displayed in Solidworks software. As shown, the fixation device 10, an orthopedic plate, spans the fracture and supports the bone. Under load, the plate bends with a degree of strain that depends upon the applied load and the stiffness of the callus. Simulated strain contours are shown on the plate It is known in the literature. Previous literature (e.g., Scientific Reports, 7:1489, 2017) shows that the degree of bending decreases as the callus stiffens. A strain gauge and circuitry are schematically shown attached to the plate. A schematic of the circuit operation are shown in FIG. 1B. The strain gauge firmly attached to the plate to transmit strain, this strain gauge is used as one leg of a Wheatstone bridge, the output of which is electrically connected to an amplifier, and a voltage to frequency converter. The output of these is fed into an LED which transmits a signal at a frequency proportional to strain on the plate. The blinking signal is collected with a photodetector and analyzed to measure the blinking frequency to determine the strain. The circuitry also requires a power source (e.g. battery, capacitor, or other source).

FIGS. 2A-2C show a demonstration of the device transmitting light through tissue in a cadaveric human tibia. FIG. 2A is a photograph of the tibia fixed with an orthopedic plate and loaded using a mechanical testing system to simulate weight bearing on the orthopedically fixed tibia. FIG. 2B shows a radiograph of the fixed tibia after osteotomy. FIG. 2C shows a Fourier transform of blinking LED signal acquired through approximately 1 cm of tissue for the intact bone before introducing an osteotomy. The optical signal was acquired with a photomultiplier tube (PMT) attached to a liquid light guide which was placed near the surface of the skin. The primary blinking frequency with a compressive load of 0 N and 350 N are only slightly shifted in frequency indicating a small but significant bending under load. FIG. 2D shows the Fourier transform of blinking optical signal acquired through tissue after introducing the osteotomy (simulating an unstable and unhealed construct). The primary blinking frequency with compressive load of 0 N (blue curve) and 350 N (green curve) are significantly displaced in frequency indicating lower stiffness. Beneficially, the approach is simple. The blinking frequency does not depend upon the wavelength of light used or the efficiency of optical collection which makes it robust.

In addition to measuring strain, there is a need for devices to measure local chemical concentrations. While electrochemical sensors could be used, optical sensors are often passive and more robust, with less less drift. Thus an object of the invention is to provide a method to measure signal from optical sensors through tissue.

Figure 3B:
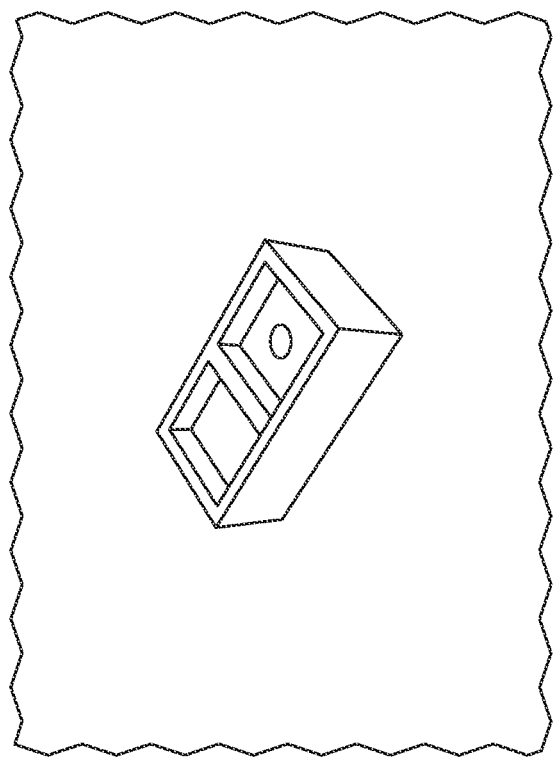
FIG. 3B is a photograph of the container which holds the LEDs in place with a chemical sensor (e.g. pH indicator) placed above each LED.
Figure 3A:
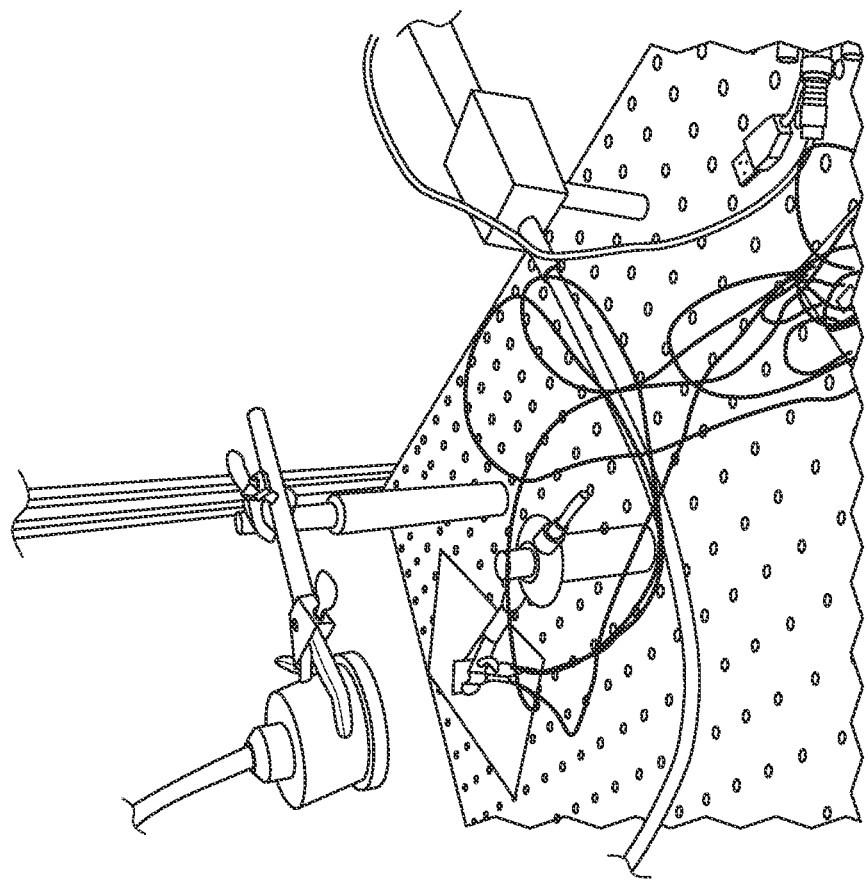
FIG. 3A is a photograph of the setup used to test the present implantable sensor, the sensor including the sensor with LED light sources, collection optics, and a photodetector to acquire the signal. Tissue can be inserted between the light source and collection optics.

FIGS. 3A-3C depicts a setup to test an embodiment of the sensor to measure chemical concentrations based on chemical indicator dyes. Two LEDs are used for telemetry, one coated with an indicator dye film, and one coated with a film containing no dye to serve as a reference. The two LEDs are held in a container which allows a film to be placed over each LED separately, and for fluid to be put on top to test chemical sensitivity, as shown in FIG. 3B. As shown in FIG. 3A, the LEDs are placed underneath collection optics, with space provided to add additional tissue between.

Figure 4B:
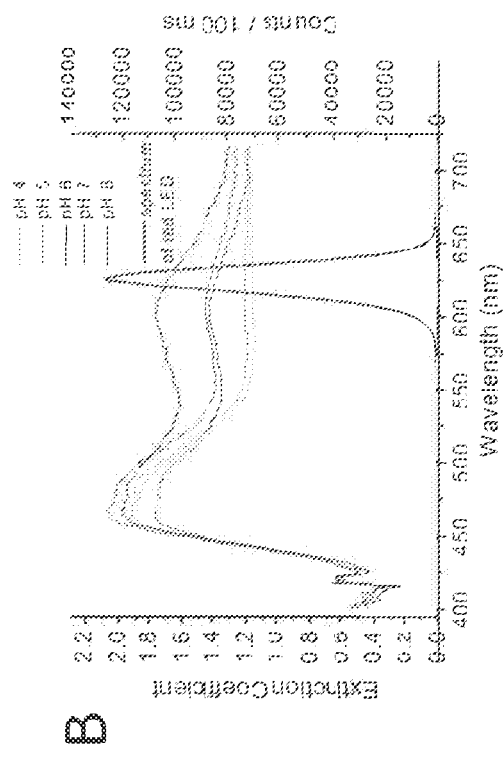
FIG. 4B is a graphical illustration of the extinction spectrum of pH paper (left axis) compared to red LED emission spectrum (right axis).
Figure 4D:
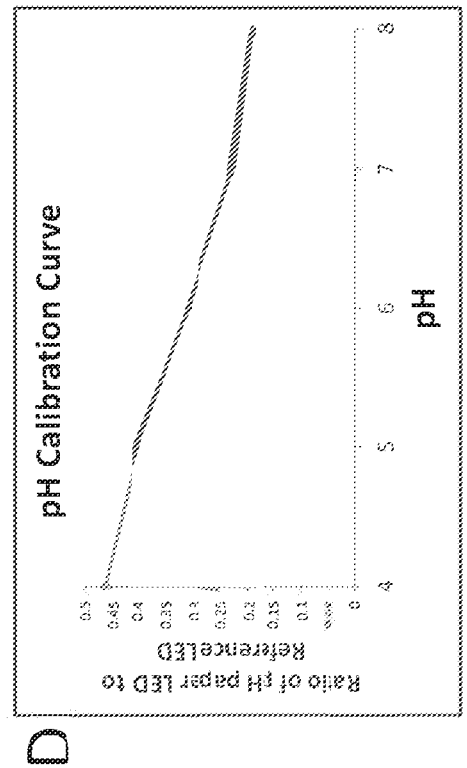
FIG. 4D is a calibration curve showing ratio of pH paper LED to the reference LED as a function of pH.
Figure 4A:
FIG. 4A is a photograph of pH paper in different buffers according to another embodiment of a sensor as disclosed herein.
Figure 4C:
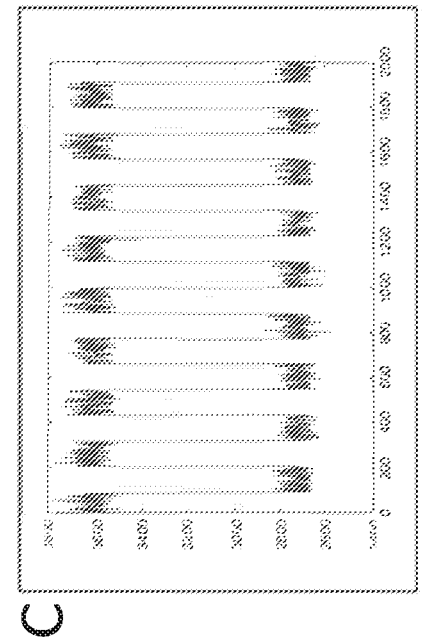
FIG. 4C is a graphical illustration of a blinking LED signal at a pH of 4, the y axis is in counts/second. The reference LED signal continuously produced an offset at ~2700 counts/s, while the blinking signal passing through the pH paper had an additional signal of ~900 counts/s.

FIGS. 4A-4C illustrates an embodiment of a sensor designed to detect pH. pH plays an important role in the pathophysiology of infection and inflammation, and is a potential biomarker for local infection. In this example, a simple pH paper is used for the pH measurement. It should be noted that a variety of other pH-sensing films in biocompatible polymer films are known in the art, such as those fabricated using polyethylene glycol (PEG), for example using formulations described in (Proc. of SPIE Vol. 10081 100810K-2, 2017). FIG. 4A shows a photograph of pH paper in different buffers. The pH causes a color change from yellow in acid to green-blue in base. FIG. 4B shows the corresponding extinction spectrum of pH paper (left axis) compared to red LED emission spectrum (right axis). As the pH increases and the paper turns green, the extinction where the LED emits at 630 nm increases accordingly and less 630 nm light penentrates. FIG. 4C shows the blinking LED signal at pH 4: the y axis is in counts/second; the reference signal is on continuously producing an offset at ~2700 counts/s, while the blinking signal passing through the pH paper has an additional signal of ~900 counts/s. This measurement was repeated in a series of standard pH buffers to generate the calibration curve, FIG. 4D. This calibration curve shows that the ratio of pH paper LED to reference LED responds strongly to pH.

Beneficially, a single photodetector can acquire both the pH indicator and reference signal, and the ratio can be used to account for variation in optical collection through the skin. In addition, using a reference with similar or overlapping wavelengths minimizes the effect of spectral differences in optical penetration through the tissue.

The present embodiments are not limited to absorption-based dyes. For example, another embodiment uses fluorescence emission from a sensor film loaded with a fluorescent indicator dye. An LED is used to excite fluorescence from the film at wavelength chosen to excite the fluorophore and generate an analyte-dependent fluorescence emission. A second LED with a wavelength similar to the fluorescence emission serves as a reference.

The present embodiments are not limited to fluorescent indicator dyes, for example, chemically responsive gels can be used to move optical elements (e.g. optical filters, mirrors, or pinholes in an analyte-dependent fashion. Stimuli-repsonsive gels and liquid crystals could also alter light polarization in an analyte or pressure-dependent fashion.

Figure 5C:
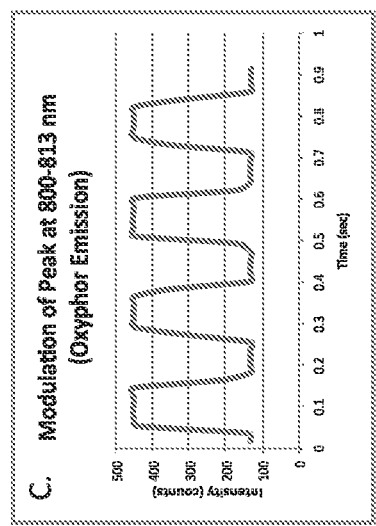
FIGS. 5A-C illustrate another embodiment of the sensor with a fluorescent indicator and reference LED which partially overlaps with the fluorescence emission.
Figure 5B:
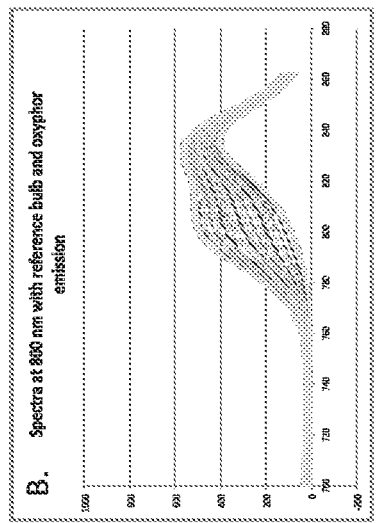
Figure 5A:
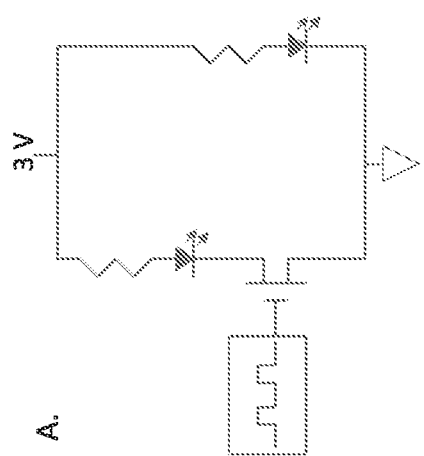

FIGS. 5A-5C illustrate another embodiment of the sensor with a fluorescent indicator and reference LED which partially overlaps with the fluorescence emission. The sensor is designed to detect oxygen because local hypoxia is a potential indicator of infection. FIG. 5A shows a circuit schematic for one near infrared LED constantly on serving as a reference, and a modulated blue LED (emitting at 460 nm) coated with an oxygen sensing film (oxyphone G4 in a polydimethylsiloxane polymer film) which is excited by the 460 nm light. The signals were collected with a spectrometer. FIG. 5B shows the resulting spectra from the constant near infrared-emitting reference bulb (emitting primarily at 835 nm) and oxyphore emission at 800 nm, with significant overlap between the two spectra. The sensor was in a hypoxic (nitrogen saturated) environment; addition of oxygen quenches the oxyphore G4 dye and reduces the modulated 800 nm signal. FIG. 5C shows the waveform of detected luminescence between 800-813 nm from FIG. 5B, including both the modulated fluorescence and constant reference. The signal and reference are clearly distinguished.

Beneficially, oxygen-sensitive dyes can be encapsulated in biocompatible polymers such as PDMS which have significant oxygen penetration. A variety of oxygen-sensitive fluorescent dyes and polymer films are known to those skilled in the art, including but not limited to ruthenium(II) Tris(bipyridine), ruthenium (II) tris(4,7-diphenyl1,10-phenanthroline) platinum octaethylporphyrin (PtOEP), platinum octaethylporphyrin ketone (PtOEPK), platinum tetrakis(4-carboxyphenyl)porphyrin (PtTCPP), palladium octaethylporphyrin (PdOEP), palladium octaethylporphyrin ketone (PdOEPK), Paladium tetrakis(4-carboxyphenyl)porphyrin (PdTCPP), paladium-meso-tetra-(4-carboxyphenyl) tetrabenzoporphyrin (oxyphor G2) iridium 2-phenylpyridine, and others. Several reviews cover oxygen sensitive dyes and polymer films, (e.g., Quaranta, Borisov, and Klimant, Bioanalytical Reviews, 2012, 4, 115-157). A preferred embodiment uses red and near infrared emitting dyes, although emission from lower wavelength emitting dyes can be converted to higher wavelengths via other layers of fluorescent dyes or quantum dots. A variety of biocompatible polymers exist to hold the dye, including but not limited to PDMS, polyvinyl chloride (PVC), polyacrylamide, polyurethane, polymethylmethacrylate (PMMA), and others.

The present embodiments are not limited to two LEDs, for example, to detect multiple analytes simultaneously additional LEDs, each modulated a unique frequencies or waveform, can be added. In addition to multiple analytes, the same analyte can be detected at multiple locations using LEDs at different positions.

To increase optical transmittance through thick tissue, the soft tissue can be mechanically compressed by pushing the collection optics against the skin. Alternatively, the output from the LEDs could be guided towards the skin using subdermal optical fibers or transparent suture wire wave guides. Putting a refractive index matching fluid or cream on the skin such as glycerol can also increase signal transmittance.

Many different photodetectors could be used. The previous two examples included a photomultiplier tube and a spectrometer hooked up to a CCD camera. Other photodetectors including phototransistors, photodiodes, and CMOS cameras could also be used. A preferred embodiment is a cell phone camera because these are ubiquitously available to physicians and patients and easily moved and programmed. For example, a cell phone camera in video mode may be used to acquire the signal from blinking LEDs through a thumb. The LEDs were closely spaced and encapsulated LEDs in a message fan. The fan was designed to display letters in the air as the fan blade spun by turning on LEDs at precise times. Although the fan was held to prevent it from spinning, a blinking signal was easily detected through tissue. The fan was chosen to show that closely spaced LEDs can be cheaply acquired and programmed; the video and analysis showed that the red signal could be easily acquired through approximately 1 cm of living tissue.

What is claimed is:

1. An implantable sensor for monitoring conditions near an implanted medical device, the implantable sensor comprising
    a power source;
    a first signal LED;
    a second reference LED;
    a circuit connected to said power source and both said first signal LED and said second reference LED, said circuit configured to modulate the light output from said first signal LED and said second reference LED with distinct modulation waveforms using power from said power source;
    an optochemical indicator configured to alter the spectrum of light incident upon it in a manner that depends upon said condition, said optochemical indicator further configured to receive light from said first signal LED without substantially receiving light from said second reference LED.

2. A system comprising an implantable medical device, the implantable sensor of claim 1 attached to the implantable medical device, and an external photodetector configured to receive light from said implantable sensor through the skin.

3. The system from claim 2, wherein said photodetector is a cell phone camera.

4. The system of claim 2, wherein said optochemical indicator comprises an absorption-based indicator dye, with said dye encapsulated in a film and said second reference LED has a similar wavelength to said first signal LED.

5. The system of claim 4 wherein said absorption-based indicator dye is a pH indicator and said condition is the local pH in proximity to said sensor.

6. The system of claim 2, wherein said optochemical indicator comprises a fluorescent indicator dye, with said dye encapsulated in a film, said first signal LED output comprising a wavelength that overlaps with said fluorescent dye excitation, and said second LED has a similar wavelength to the emission from said fluorescent indicator dye.

7. The system of claim 2, wherein said optochemical indicator comprises a fluorescent oxygen-sensitive indicator dye, with said dye encapsulated in a film, said first signal LED wavelength selected to excite fluorescence emission from said indicator film, and said second LED has a similar wavelength to fluorescence emission from said indictor film.

8. The system of claim 2 further comprising one or more additional LEDs, each said additional LEDs modulated with unique waveforms.

9. The system of claim 2 further comprising a magnetic reed switch to magnetically activate said implantable sensor.

10. The system of claim 2 further comprising a filtered photodetector to remotely activate said implantable sensor.

11. The system of claim 2 further comprising a filtered microphone to remotely activate said device using an acoustic signal, the acoustic signal comprising sound or ultrasound.

12. The system of claim 2 wherein said LEDs are separated by less than 3 mm distance.

13. The system of claim 2 wherein said implanted medical device is an orthopedic device.

14. The system of claim 2 wherein said implanted medical device is an orthopedic plate.

15. The system of claim 2 wherein said LED modulation waveform depends upon an electronic input from a strain gauge bonded to said orthopedic device.

16. A method of detecting strain on an orthopedic device comprising providing the system of claim 15, switching on said implantable sensor remotely, placing said photodetector near skin surface, acquiring and analyzing the optical signal from the device with said photodetector.

17. The method of claim 16, wherein strain is measured first with no load, and then repeated with an applied load after bearing weight on the limb fixed with an orthopedic plate.

18. The method of claim 17, wherein said applied load is measured using a bathroom scale.

19. A method of detecting conditions near an implanted medical device comprising providing the system of claim 2, switching on said implantable sensor remotely, placing said photodetector near skin surface, acquiring and analyzing the optical signal from the device with said photodetector.

* * * * *